United States Patent [19]
Cecco et al.

[11] Patent Number: 5,237,270
[45] Date of Patent: Aug. 17, 1993

[54] FERROMAGNETIC EDDY CURRENT PROBE HAVING ECCENTRIC MAGNETIZATION FOR DETECTING ANOMALIES IN A TUBE

[75] Inventors: Valentino S. Cecco; Jon R. Carter, both of Deep River, Canada

[73] Assignee: Atomic Energy of Canada Limited, Ottawa, Canada

[21] Appl. No.: 596,080

[22] Filed: Oct. 11, 1990

[51] Int. Cl.$^5$ ............... G01N 27/90; G01R 33/12
[52] U.S. Cl. ................... 324/220; 324/232; 324/242
[58] Field of Search ............... 324/219–221, 324/228, 232, 242, 243

[56] References Cited

U.S. PATENT DOCUMENTS

| | | |
|---|---|---|
| 2,124,579 | 7/1938 | Knerr et al. . |
| 2,992,390 | 7/1961 | De Witte . |
| 3,091,733 | 5/1963 | Fearon et al. . |
| 3,110,860 | 11/1963 | Allen . |
| 3,273,055 | 9/1966 | Quittner . |
| 3,483,466 | 12/1969 | Crouch et al. . |
| 3,500,181 | 3/1970 | Jackson . |
| 3,535,624 | 10/1970 | Wood . |
| 3,693,075 | 9/1972 | Forster . |
| 3,940,689 | 2/1976 | Johnson . |
| 3,940,690 | 2/1976 | Suhr et al. . |
| 4,412,177 | 10/1983 | Petrini et al. . |
| 4,477,776 | 10/1984 | Spierer ............ 324/232 X |
| 4,538,108 | 8/1985 | Huschelrath et al. ...... 324/232 |
| 4,742,298 | 5/1988 | Ando et al. . |
| 4,855,676 | 8/1989 | Cecco et al. . |

FOREIGN PATENT DOCUMENTS

| | | | |
|---|---|---|---|
| 1226901 | 9/1987 | Canada . | |
| 0130350 | 6/1987 | Japan .................... | 324/220 |
| 0948046 | 1/1964 | United Kingdom ........ | 324/220 |

*Primary Examiner*—Gerard R. Strecker
*Attorney, Agent, or Firm*—Gowling, Strathy & Henderson

[57] ABSTRACT

Eddy current probes for ferromagnetic tubes of relatively small diameters are disclosed. A probe housing is made of non-ferromagnetic material and shaped to be introduced into the tube for inspection. The probe housing includes at least two eddy current measuring assemblies either of these assemblies includes magnetic field generators for producing a maximum magnetization at a predetermined area of the tube and a minimum magnetization at a diametrically opposite area of the tube. At least one eddy current measuring coil is associated with each magnetic field generator to measure the eddy current generated in the tube and which has a relatively high sensitivity to an anomaly at the maximum magnetization area. Further the current measuring assemblies are spaced apart axially within the housing and are rotated about its central axis by a predetermined angle so that each assembly differs in sensitivity to an anomaly depending upon their location within the housing.

11 Claims, 3 Drawing Sheets

FERROMAGNETIC EDDY CURRENT PROBE HAVING ECCENTRIC MAGNETIZATION FOR DETECTING ANOMALIES IN A TUBE

FIELD OF THE INVENTION

This invention relates generally to an eddy current probe for detecting defects or anomalies in a tube made of a ferromagnetic material. In particular, the invention relates to an eddy current probe having eccentric magnetic saturation which can distinguish localized defects from concentric anomalies in a relatively small-sized ferromagnetic tube.

BACKGROUND OF THE INVENTION

Eddy current testing detects changes in eddy current induced in an object under test and is sensitive to material properties of the object through their effect on resistivity and magnetic permeability. The eddy current is indirectly measured by a probe coil located near the surface of the object which monitors the magnetic flux created by the eddy current. However, when an eddy current probe is used for ferromagnetic tube inspection, the magnetic permeability of the ferromagnetic material affects the probe coils inductance as well as depth of eddy current penetration into the material. The magnetic permeability strongly depends on factors such as:

- thermal processing history;
- mechanical processing history;
- chemical composition;
- internal stresses; and
- temperature (if close to Curie temperature).

The large variations in permeability make conventional eddy current testing for defects in magnetic materials very difficult. Thus, it is not that the eddy current probe is insensitive to a ferromagnetic material, but that is produces signals from defects as well as from permeability variation of the material. It is very difficult to analyze and separate signals by defects from those by permeability variation (permeability noise). One way of suppressing the permeability noise is to bring the magnetic material to a condition where $\mu_r = 1.0$. Relative incremental or recoil permeability, $\mu_r$, is defined as $\mu_r = \Delta B/\Delta H$ where $\Delta B$ is the change in flux density which accompanies a change in magnetizing force, $\Delta H$ created for example by an eddy current coils' alternating current.

A few slightly magnetic materials can be heated above their Curie temperature to make them nonmagnetic. Monel TM 400 heated to between 50° and 70° C. has been tested in this manner. Most materials, however, have too high a Curie temperature to be tested by this approach. The only other way to decrease $\mu_r$ to unity is by magnetic saturation.

It should also be noted that typically, the in-situ inspection of a tube in a steam generator and in other types of heat exchangers or the like, must be made from the bore of the tube, as support members such as support plates, tube sheets, headers and the like, prohibit the inspection being made from the exterior of the tube. In addition, these support members introduce various noises in eddy current signals as they modify the distribution of magnetic flux, thus affecting eddy current generation. Furthermore, quite often during the production process, these support members create certain anomalies in the tube, e.g. tube expansion under tubesheet, concentric defects, etc.

In U.S. Pat. No. 2,124,579, Jul. 26, 1938, Knerr et al describe a method of and an apparatus for testing metallic articles, in particular tubular articles. It teaches an eddy current probe located between a pair of electromagnets. In one of the embodiments, the probe and the electromagnets are made in such a way that they can be passed inside the tube under inspection.

In U.S. Pat. No. 2,992,390, Jul. 11, 1961, De Witte likewise teaches a technique of testing ferrous pipes for pipe thickness, pitting or corrosion, etc. It employs a magnetization means to magnetically saturate the pipe and a transmit-receive coil combination to measure changes in permeability which in turn correlates to pipes' physical characteristics being sought after.

U.S. Pat. No. 3,091,733, May 28, 1963, Fearon et al also describes an apparatus for detecting flaws in elongated magnetic structures. It uses a magnetizing means to magnetize the structure and subsequently a magnetic field measuring probe is passed over to measure the magnetic flux leakage that exists at the flaw.

In all these prior art techniques, the magnetic field is generated substantially coaxially with the axis of the tube under inspection. It is essential that the magnetic field is uniform around the circumference of the tube to ensure uniform sensitivity thereabout. The uniform magnetization allows the eddy current probe to pick up a localized defect in the circumference no matter what the relative location of the defect and the probe is as long as the tube under inspection is reasonably small in diameter.

U.S. Pat. No. 3,940,689, Feb. 24, 1976, Johnson, Jr. uses a combination of eddy current measurement and flux leakage detection for inspecting borehole pipes. It employs a plurality of eddy current probes positioned in circumference of the tube to pick up localized flaws in the pipe which must be fairly large in diameter. The magnetization means is also located coaxially with the pipe to ensure a uniform concentric magnetic field. However, it is very doubtful that such a magnetization means described in the patent would be strong enough to magnetize sufficiently the bore hole pipe.

There have never been convenient eddy current probes which can distinguish localized defects from concentric anomalies in a relatively small-sized ferromagnetic tube.

OBJECTS OF THE INVENTION

It is therefore an object of the present invention to provide an eddy currnt probe which can distinguish concentric anomalies in a ferromagnetic tube.

It is yet another object of the present invention to provide an eddy current probe which includes an eccentric magnetic field.

It is a further object of the present invention to provide an eddy current probe which includes a plurality of permanent magnets arranged in a specific configuration.

SUMMARY OF THE INVENTION

Briefly stated, according to the present invention, an eddy current probe for detecting anomalies in a tube made of a ferromagnetic material includes a probe housing made of a non-ferromagnetic material and shaped to be introduced into the tube for inspection and at least two eddy current measuring assemblies. The housing has an axis substantially coinciding with the axis of the tube under inspection when the probe is in use. Each of the eddy current measuring assemblies includes magnetization means for generating a magnetic field in the tube under inspection to magnetize it differently around its circumference in the plane perpendicular to the axis from the maximum magnetization at an area to the minimum magnetization at the opposite area in the circumference. Each assembly further includes at least one eddy current measuring coil to measure the eddy current generated in the tube whose sensitivity to anomaly is at the highest at the maximum magnetization area. At least two eddy current measuring assemblies are spaced apart axially and rotated about the axis from each other by a predetermined angle so that each assembly is sensitive to anomalies differently depending upon their location in the circumference.

BRIEF DESCRIPTION OF THE DRAWINGS

In a more complete understanding of the present invention and for further objects and advantages thereof, references may be made to the following description taken in conjunction with the accompanying drawings in which.

DETAILED DESCRIPTION OF PREFERRED EMBODIMENTS

Figure 1:
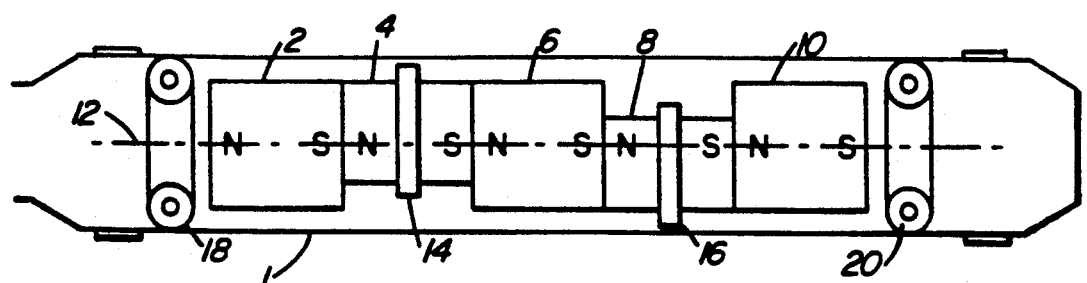
FIG. 1 is a schematic view of an eddy current probe according to one embodiment in which five cylindrical permanent magnets and bobbin type coils are used.

Referring to the accompanying drawings, FIG. 1 shows schematically one embodiment of the present invention. In the figure, five cylindrical permanent magnets 2, 4, 6, 8 and 10 are arranged end-to-end as illustrated substantially along the central axis 12 of a probe housing 1. The probe housing is not shown in the drawing but as in the prior art is made of a non-ferromagnetic material. It contains all these elements and is shaped to be introduced into a ferromagnetic tube for inspection. The axis of the probe housing substantially coincides with that of the tube under test when the probe is in use. The magnets 4 and 8 are substantially identical but smaller in diameter than the remaining substantially identical magnets 2, 6 and 10. In this embodiment, the magnets 4 and 8 have the diameter which is about 80% of that of the remaining magnets. The polarities of the magnets are arranged as shown but the smaller magnets 4 and 8 are slightly displaced off the axis of the probe housing. They are thus, in this embodiment, flush with the adjacent magnets at opposite areas in the circumference. They could be staggered more than flush for certain applications. Bobbin-type coils 14 and 16 are provided about the smaller magnets and each functions in cooperation with respective reference coil 18 or 20 as an absolute impedance probe.

The magnetic field created about each bobbin coil is therefore at the maximum in strength at the area where three adjacent magnets are flush with each other. It is at the minimum at the diametrically opposite areas in the circumference due to the opposing magnetic fields from the exposed areas of the adjacent magnet ends e.g. magnets 2 and 4. There are, therefore, in this embodiment two areas where the magnetic field strength is the highest. These maximum areas are 180° apart about the axis of the probe housing and are axially spaced apart by a predetermined distance. The minimum areas are located diametrically opposite to the respective maximum areas along the circumference.

In applicant's Pat. No. 5,117,182, there are described eddy current probes for ferromagnetic tubes which utilize eddy current measurements performed by separate coils located at positions of a different partial magnetic saturation. The saturation levels are chosen so that the only coil at the highest saturation level detects a change in the relative magnetic permeability which is an indication of the tube wall thinning but the both coils detect other anomalies which are considered as noises. By comparing the signals from the coils, it is possible to separate defects (wall thinning, baffle plates, etc.) from noises. The present invention applies this concept of using more than one different level of partial magnetic saturation around the circumference of a tube under inspection.

Figure 2:
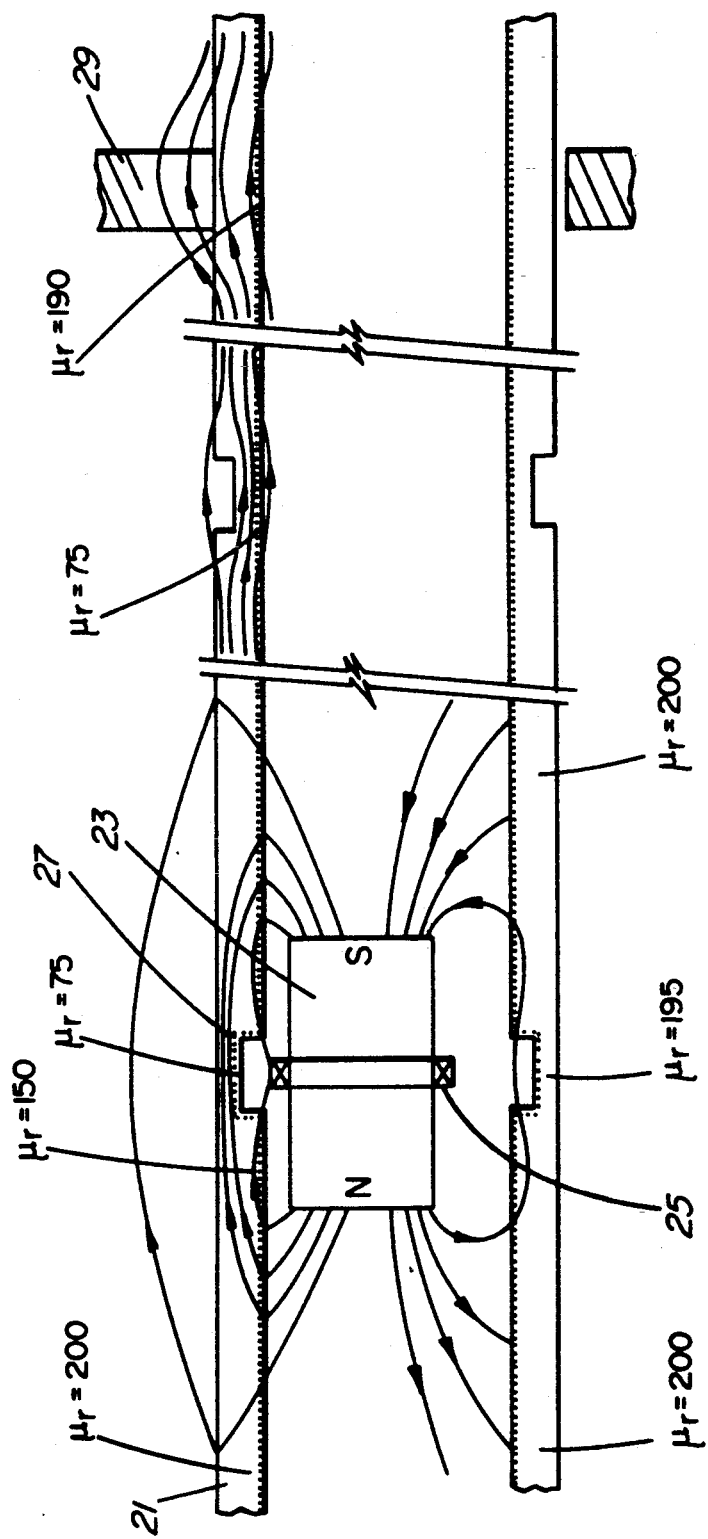
FIG. 2 is a diagrammatic illustration of the magnetic field generated by a magnet located eccentrically with the axis of a ferromagnetic tube.

In FIG. 2, it is shown the typical magnetization in a ferromagnetic tube by a magnet 23 located therein eccentrically with the axis of the tube. the relative magnetic permeability $\mu_r$ values shown are typical ones, given only as examples. As the probe is moved along the tube, passing over defects, such as interior wall thinning 27, exterior wall thinning, baffle plate 29, etc., the relative magnetic permeability $\mu_r$ in the tube wall adjacent to an eddy current measuring coil 25 (a bobbin coil in this embodiment) varies and its changes would be picked up by the coil 25.

Figure 3:
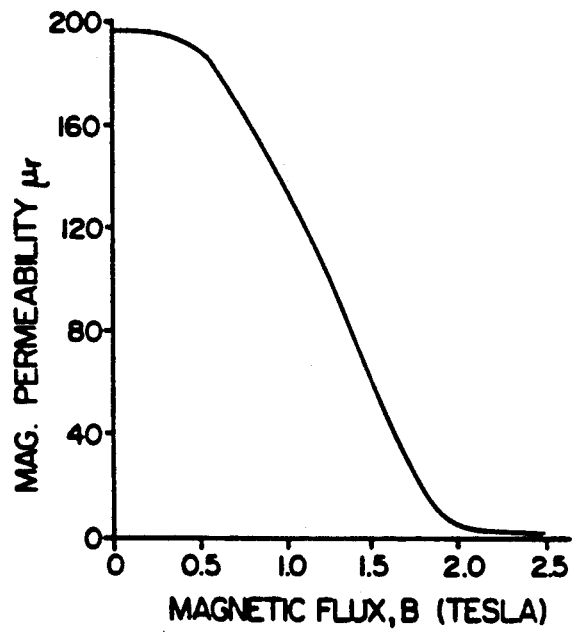
FIG. 3 is a graph showing the relationship between the relative magnetic permeability and the magnetic flux density.

FIG. 3 is a graph showing the relationship between the relative magnetic permeability and the magnetic flux for carbon steel located in a magnetic field. The values shown are typical ones and vary greatly with carbon steel samples. However, the characteristics are same. Thus in range of the partial saturation over 0.5 Tesla (i.e. B>0.5 T), typical signals from the eddy current probe would be similar to the pattern shown in FIG. 4. As shown in FIG. 3, increased flux density results in a decrease in the relative magnetic permeability. Consequently, the eddy current probe detects changes in the magnetic permeability.

Figure 4:
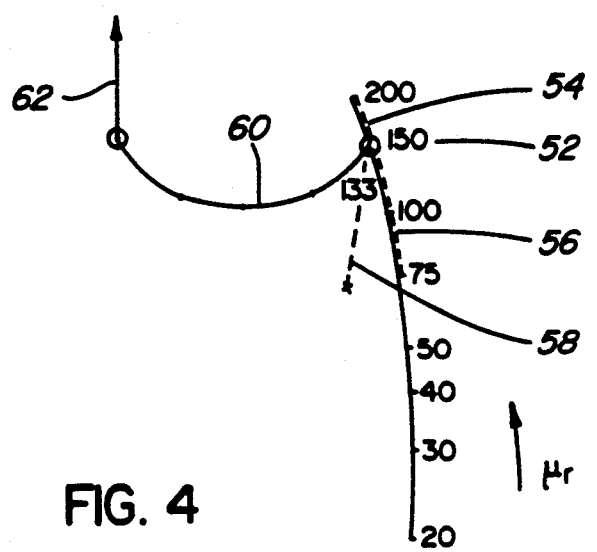
FIG. 4 depicts a typical screen display of eddy current signals.

This change in magnetic permeability $\mu_r$ is shown in FIG. 4 as an example. In this example, the testing frequency of 100 KHz was used with a bobbin probe inside a tube having an inside diameter (ID) of 13.3 mm and an outside diameter (OD) of 19.1 mm. For a normal tube under inspection the magnetic permeability $\mu_r$ equals 150 as shown at numeral 52. A baffle plate around the tube would lower the magnetic flux density and thus increase the magnetic permeability to $\mu_r=190$ shown at numeral 54. An OD (exterior wall) thinning would produce a decrease in magnetic permeability as shown by the dashed line indicated by numeral 56, while an ID (interior wall) thinning would show in addition to a $\mu_r$ decrease an additional phase variation due to a change in the tube inner diameter as shown by dashed line 58. A term known as "the fill factor" is used to represent change in the inside diameter of a tube being tested.

Hence, an increase in tube diameter represents a decrease in the "fill factor". As indicated by numeral 60 a decrease in fill factor or increase in tube inside diameter causes a change in magnetic flux density. By providing a ferrite ring, in the probe, its inductance is increased and its response is shown at numeral 62.

In a range of B<0.5 T, $\mu_r$ is constant, producing no signals responsive to changes in the flux density.

Now referring back to FIG. 2, due to the eccentricity of the toroidal magnetic field generated by the magnet 23, the eddy current probe generates a permeability signal if defects (e.g. wall thinning, baffle plates etc.) are in the area where the magnetization is above the threshold (e.g. B>0.5).

A localized defect in the tube, therefore, produces a larger eddy current signal in the coil, if it is located in a stronger magnetic field. In other words, the sensitivity of the eddy current measuring coil is the highest at the maximum magnetic field strength area. The present invention resides in the idea of placing the areas of the maximum and minimum magnetic field strengths in specific configurations. Therefore as shown in FIG. 1, because the maximum areas are 180° apart about the axis, a concentric defect or anomaly produces in the both coils 14 and 16 signals of an equal magnitude as the coil is passed over it, while a localized defect produces unequal signals in the coils. Therefore, by monitoring the two signals, it is possible to distinguish concentric anomalies from non-concentric ones.

Figure 5:
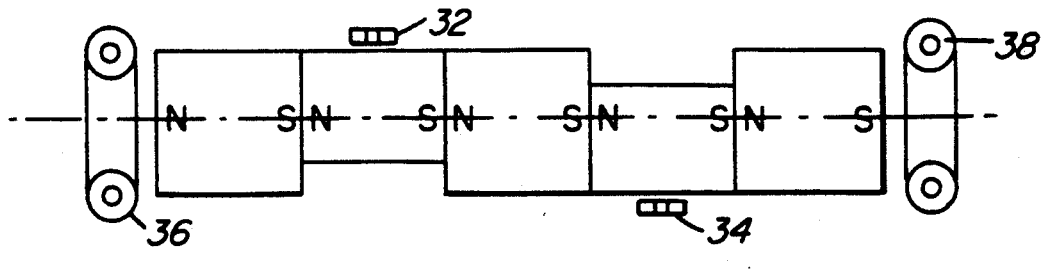
FIGS. 5, 6 and 7 illustrate schematically further embodiments of the invention where different coil configurations are used.

In FIG. 5 another embodiment is illustrated schematically. The embodiment uses pancake-type coils 32 and 34 for eddy current measuring means, each of which is located at the respective maximum magnetic field strength area. The magnet configuration is the same as that shown in FIG. 1. The coils function as the absolute impedance mode in cooperation with respective reference coils 36 and 38.

Figure 6:
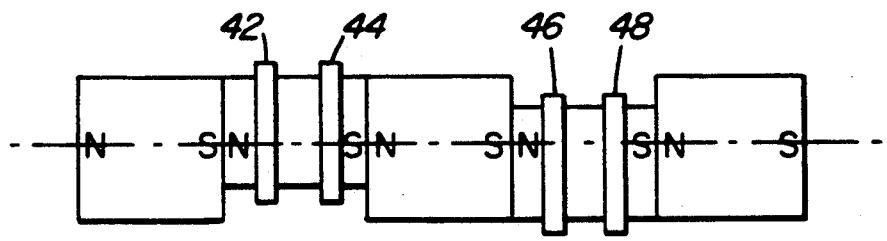

It is also possible to employ eddy current probes in the differential mode in place of the absolute impedance probes of the earlier embodiments. Therefore, as shown in FIG. 6, two pairs of bobbin coils 42,44 and 46,48 are positioned over the smaller magnets of the same magnet arrangement of FIG. 1. Because the probes are of the differential mode type, no reference coils are needed.

Figure 7:
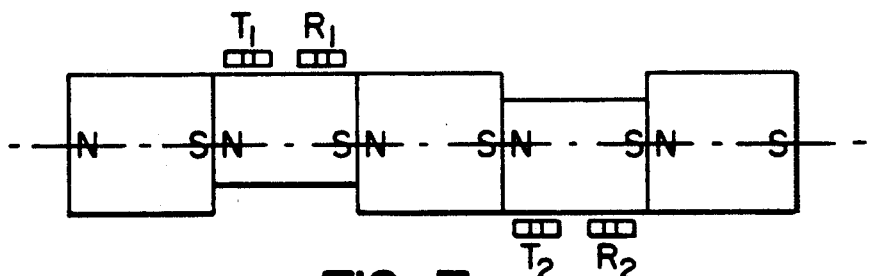

Eddy current probes in the transmit-receive configuration can also be used as another embodiment which is shown in FIG. 7. A pair of transmit coils and receive coils are positioned at the respective maximum areas. The transmit coils are designated by T and the receive coils by R. Typically, the distance $t_o$ between the transmit and receive coils is equal to or larger than the thickness of the tube wall.

Figure 8:
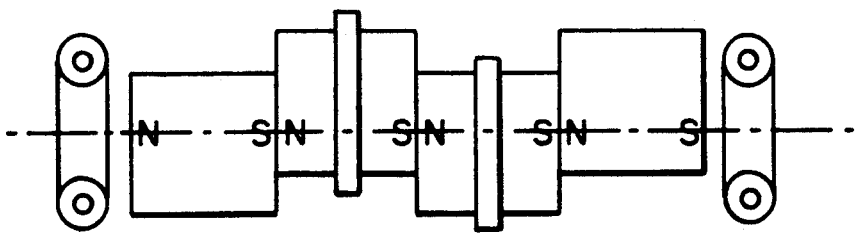
FIG. 8 is yet another embodiment of the invention in which four permanent magnets are used to generate a specific magnetic field.

Turning to FIG. 8, there is illustrated another embodiment of the present invention. In this embodiment, four substantially identical cylindrical permanent magnets are arranged end-to-end substantially along the axis of the probe housing. However, each adjacent magnet is oppositely displaced off the axis by a predetermined amount which in this embodiment is about 5% of the diameter of the magnet. The eddy current measuring coils are located on the middle magnets as shown.

Figure 9:
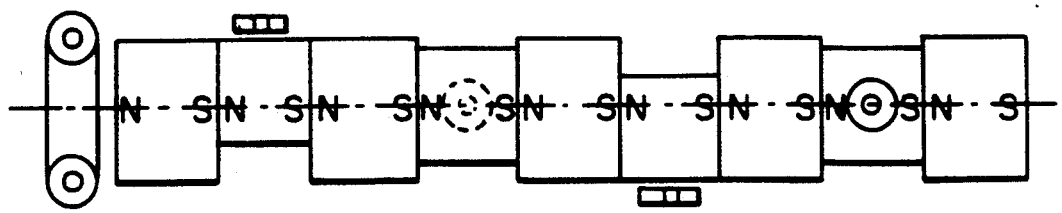
FIG. 9 is a still further embodiment of the invention in which four eddy current measuring coils are used.

It is also possible to employ four eddy current measuring assemblies whose highest points of sensitivity are displaced angularly about the axis about 90° apart from each other. This configuration is shown in FIG. 9.

We claim:

1. An eddy current probe for detecting anomalies in a tube made of a ferromagnetic material, comprising:

a probe housing made of a non-ferromagnetic material and shaped to be introduced into the tube for inspection, said housing having a central axis substantially coinciding with the axis of the tube to be inspected when the probe is in use;

at least two eddy current measuring assemblies provided in said housing, each said assembly including magnetization means for generating a magnetic filed in the tube under inspection to magnetize said tube, said magnetization means producing a maximum magnetization at an area of said tube and a minimum magnetization at a diametrically opposite area of said tube and at least one eddy current measuring coil associated with said magnetization means to measure the eddy current generated in the said tube and which has a relatively high sensitivity to an anomaly at said maximum magnetization area; and said eddy current measuring assemblies being spaced apart axially within said housing and rotated about said central axis from each other by a predetermined angle so that each assembly is sensitive to anomalies differently depending upon their location in said housing.

2. The eddy current probe, according to claim 1, wherein:

said eddy current measuring assemblies are two in number, said magnetization means including five cylindrical permanent magnets arranged end-to-end along said central axis, the second and the fourth magnets being smaller in diameter than the remaining magnets and being oppositely diametrically displaced off the central axis by a predetermined amount, and said eddy current measuring coils are positioned on the said second and the fourth magnets.

3. The eddy current probe, according to claim 1, wherein:

said eddy current measuring assemblies are two in number, said magnetization means including four substantially identical cylindrical permanent magnets, arranged end-to-end substantially along said central axis, each adjacent magnet being oppositely displaced off said central axis by a predetermined amount, and said eddy current measuring coils are positioned on the middle magnets.

4. The eddy current probe according to claim 2, wherein said eddy current measuring coils are of the impedance measuring type and comprise bobbin type coils wound about the respective magnets.

5. The eddy current probe according to claim 2, wherein said eddy current measuring coils are of the impedance measuring type and comprise pancake type coils positioned at the respective maximum magnetization areas.

6. The eddy current probe according to claim 4, wherein said coils are two in number in each of the said assembly and are connected in the differential operation mode.

7. The eddy current probe according to claim 5, wherein said coils are two in number in each of the said assembly and are connected in the differential operation mode.

8. The eddy current probe according to claim 2, wherein
said eddy current measuring coils are of the transmit-receive type and comprise pancake type coils positioned at the respective maximum magnetization areas.

9. The eddy current probe according to claim 2, wherein
said diameter of the second and fourth magnets is about 80% of the diameter of the remaining magnets.

10. The eddy current probe according to claim 3, wherein
said predetermined amount is about 5% of the diameter of the magnets.

11. The eddy current probe according to claim 1, wherein:
said eddy current measuring assemblies are four in number and located in line along the central axis of the probe housing, and
each of the assemblies has an area about the circumference of said probe housing where the sensitivity is a maximum, and
the areas of maximum sensitivity of said assemblies are angularly displaced about said central axis by about 90°.

* * * * *